United States Patent [19]

Zimmermann et al.

[11] 4,350,767

[45] Sep. 21, 1982

[54] METHOD FOR ISOLATING AND PURIFYING ENZYMES FROM A CRUDE ENZYME SOLUTION

[75] Inventors: Ulrich Zimmermann, Jülich, Fed. Rep. of Germany; Mohammed Saleemuddin, Aligarh, India; Günter Pilwat, Niederzier, Fed. Rep. of Germany

[73] Assignee: Kernforschungsanlage Jülich Gesellschaft mit beschränkter Haftung, Jülich, Fed. Rep. of Germany

[21] Appl. No.: 264,022

[22] Filed: May 15, 1981

Related U.S. Application Data

[63] Continuation-in-part of Ser. No. 51,197, Jun. 22, 1979, abandoned.

[30] Foreign Application Priority Data

Jun. 28, 1978 [DE] Fed. Rep. of Germany ....... 2828235

[51] Int. Cl.$^3$ .......................... C12N 9/00; C12N 9/04
[52] U.S. Cl. .................................. 435/183; 435/190; 435/815
[58] Field of Search ............... 435/183, 190, 814, 815; 260/112 B

[56] References Cited

U.S. PATENT DOCUMENTS 4,136,161  1/1979  Falkowski et al. ............... 424/75 X

OTHER PUBLICATIONS

Ihler et al., "Enzyme Loading of Erythrocytes", Proc. Nat. Acad. Sci., vol. 70, No. 9, pp. 2663-2666, (1973).
Chang, "Microencapsulation of Enzymes and Biologicals", in Methods in Enzymology, vol. 44, pp. 201-218, (1976).

*Primary Examiner*—Lionel M. Shapiro
*Attorney, Agent, or Firm*—Becker & Becker, Inc.

[57] ABSTRACT

A method and adsorption medium for isolating and purifying enzymes from a crude enzyme solution of animal organs or tissues. An adsorption medium for bringing about the binding of a predetermined enzyme is introduced into the crude enzyme solution and is left therein until the binding takes place, whereupon the adsorption medium is removed from the crude enzyme solution and the enzyme is separated from the adsorption medium by extraction or elution with a suitable solution. The adsorption medium is in the form of membranes of human or animal erythrocytes which have been hemolyzed by osmosis. Those enzymes which have the same or nearly the same affinity as regards binding on the membranes as does the predetermined enzyme which is to be bound are separated from the membranes prior to introducing the membranes into the crude enzyme solution. The amount of the enzymes first removed that is bound being less than the amount of erythrocytes used to form the membranes.

6 Claims, No Drawings

METHOD FOR ISOLATING AND PURIFYING ENZYMES FROM A CRUDE ENZYME SOLUTION

This is a continuation-in-part of co-pending application Ser. No. 51,197-Zimmermann et al filed June 22, 1979, abandoned.

BACKGROUND OF THE INVENTION

Field of the Invention

The present invention relates to a method of isolating and purifying enzymes from a crude or unrefined enzyme solution of animal organs or tissues. According to this method, an adsorption medium for bringing about the aggregation or binding of a predetermined enzyme is introduced into the crude enzyme solution and is left therein until the binding takes place, whereupon the adsorption medium is removed from the crude enzyme solution and the enzyme is separated from the adsorption medium by extraction or elution by means of a suitable solution. The present invention also relates to an adsorption medium for carrying out this method.

TECHNICAL CONSIDERATION AND PRIOR ART

Enzymes are used in many fields, for example, clinical chemistry, foodstuff chemistry, botany, microbiology, pharmacology, as well as agricultural chemistry. For this purpose, specific enzymes, and particularly in highly purified form, are often required.

A method of the above mentioned type is known, according to which an adsorption medium, such as diatomite, aluminium oxide, kaolin, or molecular filters, are used. It is also possible pursuant to this known method to obtain a certain degree of purity of predetermined enzymes. However, it is not possible by using the above mentioned adsorption or binding medium to obtain a specific enzyme in highly pure form with a single adsorption and elution. This is so because a preferred adsorption of a predetermined enzyme or diatomite is practically impossible.

For this reason, further methods for separating complex enzyme mixtures were also developed; these methods utilize high voltage electrophoresis, electrodialysis, or also chromatography. However, such methods are relatively expensive.

A publication of Ihler et al titled "Enzyme Loading of Erythrocytes" in "Proceedings of the National Academy of Science"; Vol. 70, No. 9 pp. 2633 to 2666 (1973) discloses an approach for using erythrocyte "ghosts" to encapsulate enzymes. However, the method of Ihler et al is not at all related with the production of an adsorption medium for particular enzymes of with a method concentrating enzymes from a solution containing the enzyme by means of an adsorption medium. Moreover, Ihler et al discloses healing after hemolysis and not with a further treatment of erythrocytes to provide ruptured membranes. In Ihler et al, the enclosure of the enzyme occurs in minutes during the course of the hemolysis while with the method according to the present invention the hemolysis is already concluded before utilization of the erythrocytes as an adsorption medium.

SUMMARY OF THE INVENTION

It is therefore an object of the present invention to provide a method of the above mentioned general type by means of which it is possible to isolate a predetermined enzyme from a crude enzyme solution and to produce it in a highly purified form. It is a further object of the present invention to provide an adsorption medium which can be used to carry out this method.

DESCRIPTION OF THE PREFERRED EMBODIMENT

The objectives of the present invention are met by a method of the above described general type in which adsorption medium, in the form of membranes of human or animal erythrocytes, which have been hemolyzed in a known manner by osmosis, is introduced into the crude enzyme solution. The membranes are used in their ruptured states. In this connection, first those enzymes are separated from the membranes which (enzymes) have the same or nearly the same affinity as regards their binding on the membranes as the affinity of the enzymes which are to be bound.

The present invention concerns the use of enzyme-depleted membane shreds, ruptured membranes or membrane material for the isolation or desired enzymes from a crude enzyme solution.

It is known that enzymes in the animal body are transported while being attached to cell membranes, the release of these enzymes being controlled by the environmental conditions, i.e., the deposit or accumulation and release of enzymes are determined by the state of ambient solution. This cell membrane material would operate somewhat analogous to an ion exchanger.

For attaining depleted membrane materials erythrocytes are hemolyzed and then elutriated with respect to enzymes normally attached to the cell, especially with respect to enzymes having at least nearly the same affinity to the membrane material as the desired enzymes. In practice, a proteinic enzyme, e.g., of special origin—perhaps from the brain of a sheep—can thus be isolated selectively using membranes of human enzyme (which is normally associated with the erhthrocytes). The proportions of membrane material to solution and the enzyme concentration of the latter are not at all critical.

The method of the present invention is simple to carry out and is moreover inexpensive, because animal blood or outdated human blood can be used, and the membranes can be repeatedly used as adsorption medium. In addition, it has been found that already with a single adsorption and elution, enzymes are isolated and can be produced in highly pure form.

An expedient variation of the method of the present invention comprises that the enzymes of the same or nearly the same affinity can be separated by means of the solution provided for the elution from the membranes prior to their introduction into the crude enzyme solution. When repeatedly using the membranes as adsorption medium, no special preparation step is necessary prior to introducing the adsorption medium into the crude enzyme solution.

The adsorption medium of the present invention is characterized primarily in that it consists of membranes which are formed from human or animal erythrocytes which are already hemolyzed in a known manner by osmosis. The volume or amount of enzymes which are bound on the membranes, and which have the same or nearly the same affinity as the enzyme to be bound with regard to adsorption on the membranes, is or should be less than the volume or amount corresponding to the erythrocytes used to form the membranes. Consequently, there is provided an adsorbent for use in the isolation of an enzyme in purer form from a crude enzyme solution comprising membranes formed from hemolyzed human or animal erythrocytes which membranes have combined with them a lesser quantity of enzymes having the same or substantially the same affinity in regard to their combination with the membranes as the enzyme to be isolated, than the quantity in the erythrocytes used for the formation of the membranes.

The membranes already formed during the hemolysis can be stored and used for many days. Nevertheless, it may be expedient to stabilize the membranes by means of at least one cross-linking medium, such as glutardialdehyde, in order in this way—without having to make allowance for a reduction in the affinity of the enzyme to be isolated—to obtain a prolongation of the storage time for the membranes by about a factor of two. For this purpose, the membranes can be treated further with a solution containing 1 mM/l glutardialdehyde.

PREPARATIONS

Hemolysis of erythrocytes to form membranes:

The starting material was fresh human blood, outdated human blood from bloodbanks, or blood from rats, cattle, or pigs. The erythrocytes were washed two times with an isotonic NaCl solution. The washed erythrocytes were introduced in a volume ratio of 1:40 into a buffer solution containing 5 mM/l phosphate and having a pH value of 8.0 at 4° C. After the hemolysis, the suspension was centrifuged for thirty minutes at 4° C. at 15,000 times the acceleration of gravity. The membranes formed were then washed two times with the above mentioned buffer solution in the same mixture ratio in order to remove the hemoglobin. The resulting membranes are in a ruptured, unhealed state.

Prepartion of the adsorption medium for isolating and purifying the enzyme aldolase as well as the enzyme glyceraldehyde-3-phosphate-dehydrogenase (GAPDH):

The membranes formed by hemolysis of the erythrocytes were suspended in a volume ratio of 1:20 at 4° C. in a 2% NaCl solution which contained 5 mM/l phosphate; the suspension was stirred for one hour. The membranes were then centrifuged and washed two times with the above mentioned solution. The membranes were subsequently washed one time with a buffer solution containing 5 mM.l phosphate and having a pH value of 8.0.

Preparation of the crude enzyme solution:

Crude enzyme solutions were prepared which were respectively separated from muscles, livers, kidneys, and brains of mice and rats. For this purpose, 2 g of the respective specimens were reduced to small pieces for 30 seconds with an Ultra-Turrax-Homogenizer, and were subsequently homogenized for two minutes in a Potter-Elvehjem-Glass-Homogenizer, which was equipped with a Teflon pestle and contained a buffer solution containing 5 mM/l phosphate and 10 mM/l β-mercaptoethanol. The volume of the homogenate was brought to 40 ml, and the homogenate was stirred for one hour at 4° C. and subsequently centrifuged for 45 minutes at about 15,000 times the acceleration of gravity. To recover the crude enzyme solution, the supernatant was filtered through a membrane filter having a pore diameter of 0.4 μm.

EXAMPLE I

Adsorption medium prepared from human erythrocytes was incubated in a volume ratio of 1:3 in a crude enzyme solution formed of mice muscles, and was left in the solution for about one hour. The membranes were then washed two times at 4° C. with a buffer solution containing 5 mM/l phosphate. Subsequently, to isolate aldolase, the membranes were incubated in a volume ratio of 1:20 at 4° C. in a buffer solution containing 5 mM/l phosphate, 15 mM/l NaCl, and 2 mM/l fructose-1, 6-diphosphate, and having a pH value of 8.0. The thus formed suspension was agitated for 30 minutes in an ice bath. The membranes were then centrifuged off.

The determination of the aldolase activity was carried out pursuant to the method of Sibley and Lehninger (Sibley, J. A. and Lehninger, A. L., J. Biol. Chem. 177, 859–872 (1949).

While the specific activity of the aldolase in the crude enzyme solution was 0.01 units per mg protein, the activity after elutriation was 0.1 units per mg protein.

EXAMPLE II

As in Example I, adsorption medium prepared from human erythrocytes were, in a volume ratio of 1:3, incubated in a crude enzyme solution formed of mice muscles, and were left in the solution for about one hour. The membranes were then washed with a buffer solution containing 5 mM/l phosphate, 15 mM/l NaCl, and 2 mM/l fructose-1, 6-diphosphate, and having a pH value of 8.0. The thus formed suspension was agitated in an ice bath for about 30 minutes. To elute the enzyme GAPDH, the membranes were introduced and left for 90 minutes in a solution containing 5 mM/l phosphate and 2 mM/l reduced nicotinamide adenine dinucleotide. The membranes were then centrifuged off.

The determination of the GAPDH was carried out pursuant to the method of Tanner and Gray (Tanner, M. J. A. and Gray W. R., Biochem, J. 125,1109–1117 (1971).

While the specific activity of the GAPDH in the crude enzyme solution was 7.4 units per mg protein, the specific GAPDH activity after elutriation was 153 units per mg protein.

As a control, a further purity determination of the enzyme GAPDH was carried out with a specimen of the enzyme coated membranes. In this connection, the suspending of the membranes, the polyacrylamide gel electrophoresis in the presence of SDS, and the staining were carried out pursuant to the method of Fairbanks et al (see Fairbanks, G., Steck, T. L., and Wallach, D. F. H., Biochemistry 10, 2606–2617 (1971)). During the gel electrophoresis, the enzyme GAPDH appeared as the single band, to which could be assigned a molecular weight of 37,000, which corresponds very closely to other values from the pertinent literature.

EXAMPLE III

As described in Example I, the enzyme aldolase was isolated and purified. In contrast to Example I, a crude enzyme solution prepared from the livers of mice was used. The specific activity of the aldolase enzyme contained in the crude enzyme solution was 0.01 units per mg protein, while the specific activity of the enzyme after elutriation was 0.1 units per mg protein.

EXAMPLE IV

As described in Example II, the enzyme GAPDH was isolated and purified. In contrast to Example II, a crude enzyme solution prepared from the livers of mice was used. The specific activity of the GAPDH enzyme contained in the crude enzyme solution was 1.1 units per mg protein, while the specific activity of the enzyme after elutriation was 90 units per mg protein.

EXAMPLE V

As described in Example II, the enzyme GAPDH was isolated and purified. In contrast to Example II, a crude enzyme solution prepared from the kidneys of mice was used. The specific activity of the GAPDH enzyme contained in the crude enzyme solution was 1.0 units per mg protein, while the specific activity of the enzyme after elutriation was 146 units per mg protein.

EXAMPLE VI

As described in Example II, the enzyme GAPDH was isolated and purified. In contrast to Example II, a crude enzyme solution prepared from the brains of mice was used. The specific activity of the GAPDH enzyme contained in the crude enzyme solution was 3.3 units per mg protein, while the specific activity of the enzyme after the elutriation was 144 units per mg protein.

EXAMPLE VII

As described in Example II, however, using a crude enzyme solution prepared from the muscles of rats, the enzyme GAPDH was purified with the same results as given in Example II.

EXAMPLE VIII

The same method as described in Example IV was followed. However, the membranes prepared for the isolation were, prior to their incubation in the crude enzyme solution, incubated for ten minutes, for their cross-linking, in a buffer solution containing 5 mM/l phosphate and 1 mM/l glutardialdehyde. Subsequently, the membranes were centrifuged and were washed two times with a buffer solution containing 5 mM/l phosphate and having a pH value of 8.0. The same results as those given in Example IV were obtained.

The adsorption medium is characterized by an affinity for the enzyme to be bound which is higher than the corresponding affinity of the quantity of erythrocytes needed for formation of the adsorption medium. This does not include any explicite recitation how many erythrocytes are needed for binding the adsorption medium in order to bind a particular enzyme. This however is not necessary with a view toward putting an average man skilled in the art in a position to carry out the teaching in accordance with the present invention. Moreover, since the adsorption medium is useable in repeated extent for rectification of a particular quantity of enzymes there need not adsolutely be utilized a particular quantity of adsorption medium. The rectification of the provided quantity of enzymes can be undertaken much more by repeated utilization or application of the adsorption medium also under such circumstances when the affinity of the adsorption medium is small for a particular enzyme.

The effectiveness of the adsorption medium respectively the height or level of the affinity for a particular enzyme additionally can be determined by an average man skilled in the art by way of simple test attempts whereby the average man skilled in the art for example can proceed on the basis of statements provided in the sample embodiments about the utilized quantity of erythrocytes. For this purpose, attention is directed to the fact that the adsorption medium comprises practically the centrifuged membranes of the hemolized erythrocites (aside from the elutriation on the one hand) and that the membranes have been incubated in the raw-enzyme-solution in a volume ratio of 1:3 according to the statements in the sample embodiments.

What we claim is:

1. A method of isolating and purifying selected enzymes from a crude enzyme solution made from animal organs or tissues, the method including the steps of:
    contacting the crude enzyme solution with an adsorption medium composed of hemolyzed, ruptured, erythrocyte membranes, the membranes having an affinity to bind by adsorption the selected enzymes thereto, to thereby adsorb the selected enzyme on the membrane;
    removing the membranes from contact with the crude enzyme solution with the selected enzymes adsorbed on the membranes, and
    separating the selected enzyme from the membranes by elution.

2. The method of claim 1 wherein the membranes are obtained from mamalian erythrocytes.

3. A method of isolating and purifying selected enzymes from a crude enzyme solution of mamalian tissue, the method including the steps of:
    preparing an adsorption medium by hemolyzing mamalian erythrocytes to provide ruptured erythrocyte membranes;
    preparing a crude enzyme solution including a selected enzyme from mamalian tissue;
    introducing the adsorption medium including the ruptured erythrocyte membranes into the crude enzyme solution;
    leaving the ruptured erythrocyte membranes in the solution for a sufficient time to absorb the selected enzyme on the membranes;
    washing the membranes with a buffer solution;
    removing the selected enzyme from the membranes and isolating the selected enzymes in a buffer solution suspension, and
    removing the membranes from the suspension.

4. The method of claim 3 further including the step of stabilizing the membranes by exposing the membranes to a cross-linking medium prior to introducing the adsorption medium to the crude enzyme solution.

5. The method of claim 2 wherein the cross-linking medium is glutardialdehyde.

6. The method of claim 1, 2, 3, 4 or 5 wherein the selected enzyme is from the group consisting of aldolase and glyceraldehyde-3-phosphate-dehydrogenase (GAPDH).

* * * * *